United States Patent

Plant Pat. 3,842

Patented Mar. 16, 1976

3,842

*PASPALUM VAGINATUM* GRASS PLANT

Hubert F. Whiting, Indio, Calif., assignor to Nan Hutchinson, Phoenix, Ariz., and Hubert F. Whiting, Indio, Calif., fractional part interest to each Filed May 2, 1974, Ser. No. 466,265

Int. Cl. A01h 5/12

U.S. Cl. Plt.—88 1 Claim

The present invention relates to a new and distinct variety of *Paspalum vaginatum* grass which was discovered by me growing under cultivation on a golf course located at Point Lansdale in Victoria, Australia.

This new variety was being watered with water having a very high salt content, at least 6000 parts per million. However, this new variety was growing quite well and had a much better green color than the Bermuda grass growing in the same area, which was light brown. The new *Paspalum vaginatum* variety also had much better wearing qualities than the Bermuda. The area in which both grasses were growing was a golf course tee area which had almost constant traffic.

A sod of this new *Paspalum vaginatum* variety was obtained by me and transplanted into a nursery at another golf course in Australia. As soon as this sod grew sufficiently, I broke off stolons and replanted them so as to cover a larger area, which eventually spread and covered rapidly.

Following the experiments described above, stolons of this new *Paspalum vaginatum* variety were planted at a sod farm located in Indio, Calif. The stolons were planted on 18" centers and produced complete ground cover in 50–60 days. Bermuda grass growing in the test area was crowded out. Growth rate tests confirmed that the new *Paspalum vaginatum* variety grew at roughly twice the rate of Bermuda in the same test area. Further salt-resistance tests were performed which confirmed my initial observations. As a result of the tests and experiments at Indio, Calif., it has also been discovered that the new *Paspalum vaginatum* variety has a surprising and marked ability to withstand extremely cold temperatures. For example, it was observed that only 10 days after exposure to severe frost conditions (nighttime temperature of 16° F.), the new variety had completely recovered and exhibited its normal appearance.

When mowed to a height of approximately 3/16", the test plot of the new variety at Indio, Calif., formed a very desirable surface for a golf putting green.

Continued asexual reproduction by strong rhizomes and stolons have confirmed that the above-described characteristics are transmitted through succeeding propaga-
lowing unique combination of characteristics:
lowing unique combinatio of characteristics:

(a) An attractive, deep-green color;

(b) The plant is low-growing and erect in habit, spreading by rhizomes and stolons;

(c) The stolons contain many nodes, forming dense matted patches;

(d) Culms vary in height from 12–43 cm.;

(e) The leaves are folded in bud shoot;

(f) The blades are flat with the upper blade surface deeply ridged. The blades are glabrous except at the base of older leaves where 1–20 hairs are present near the ligule;

(g) The blades are slender, gradually tapering to an acute point. The first mature leaf is 2–4 mm. in width and 80–120 mm. in length.

(h) The ligule is membranous, truncate to extremely acute, medium in height;

(i) Auricles are absent;

(j) The collar is broad, distinct, glabrous, somewhat constricted and the midvein slightly visible;

(k) The sheath is smooth, split (margins generally overlapping, then opening again near the node), glabrous, compressed, and the midvein is prominent;

(l) The hairs are few and are connected in two places: (i) on the inside of the collar at the base of the ligule, and (ii) where the ligule, sheath and collar meet;

(m) The internodal space on the stolons are 5–7 cm., and on the culms, the internodal space is 2–4 cm. apart;

(n) The inflorescence consists of two paired spikes at the top of the main stem, which is deflexed at maturity and from 25–35 mm. long;

(o) The spikelets are glabrous, in two rows, elliptical, 2–4 mm. long, blunt at their base, pointed at their tips, with glumes present; and (p) The spikelets are sterile with three stamens and two styles, when present.

DESCRIPTION OF CLOSEST KNOWN VARIETY OF THE SPECIES

By comparison, the closest known variety of the species is only somewhat erect in habit and tends to spread mainly by stolons containing many nodes about 20–30 mm. apart. The culms of the closest known variety of the species vary in height from 30–150 mm. The first mature leaf of the closest known variety is 2–3 mm. wide and 30–50 mm. long and the ligule is rather small and with many hairs. The margins of the split sheath of the closest known variety generally overlap all the way to the node. The internodal space on the stolons of the closest known variety is 2–3 cm. and on the culms the internodal space is 1–1.5 cm.

The claimed *Paspalum vaginatum* grass plant is illustrated in the accompanying color photographs, in which:

Figure 1:
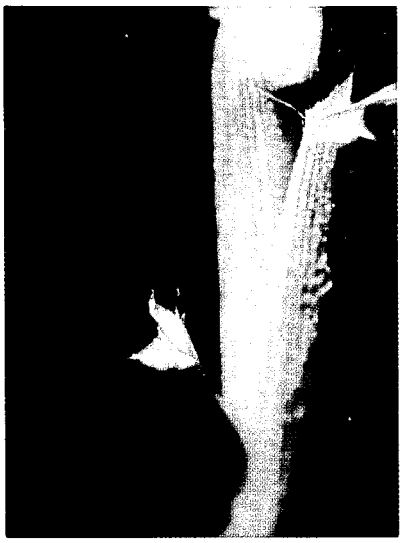
FIG. 1 is a photomicrograph (approximately 10×) showing hairs protruding from the base of the ligule.
Figure 2:
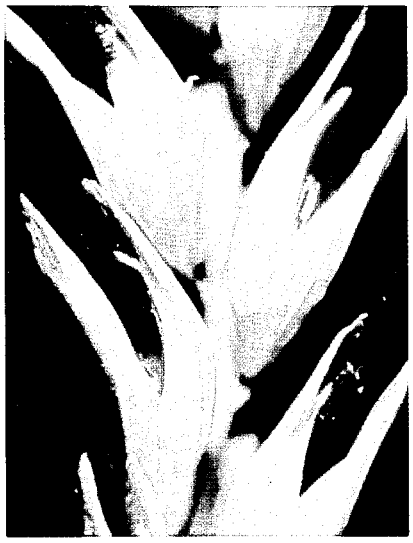
FIG. 2 is a photomicrograph (approximately 30×) showing the spikelets.
Figure 3:
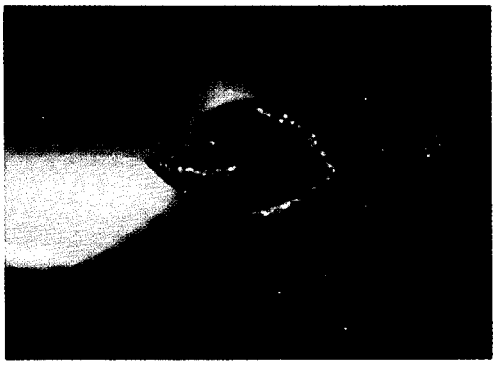
FIG. 3 and FIG. 4 are photomicrographs (approximately 30×) showing the leaves folded in bud.
Figure 4:
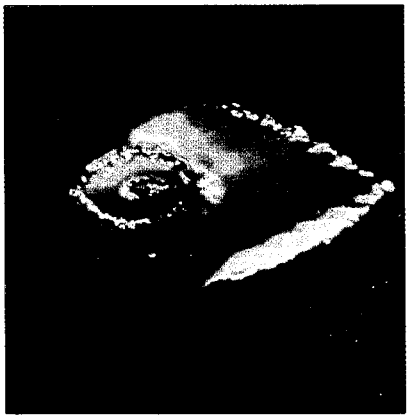
Figure 5:
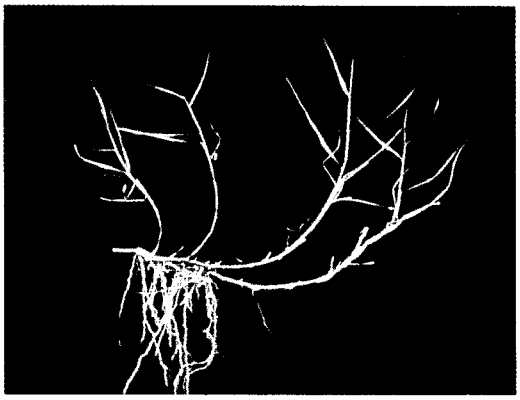
FIG. 5 is a photograph illustrating the new plant's erect habit.
Figure 6:
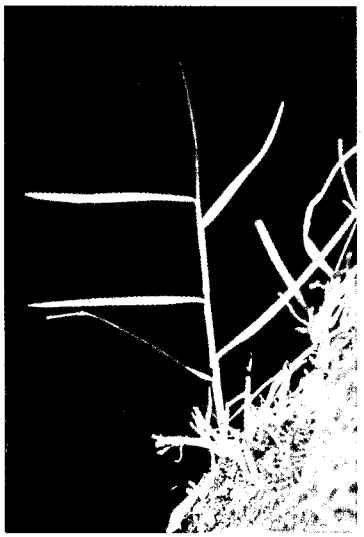
FIG. 6 is a photograph depicting the flat leaf blades.
Figure 7:
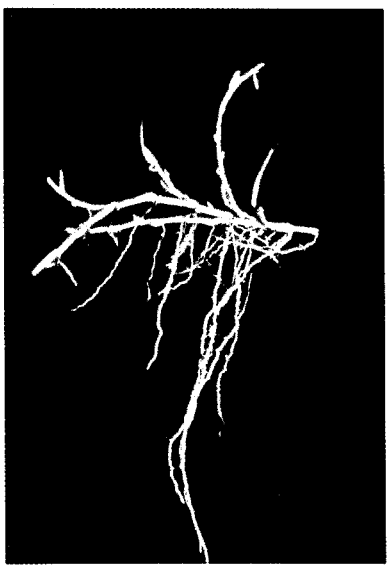
FIG. 7 is a photograph depicting the vigorous rhizome.
Figure 8:
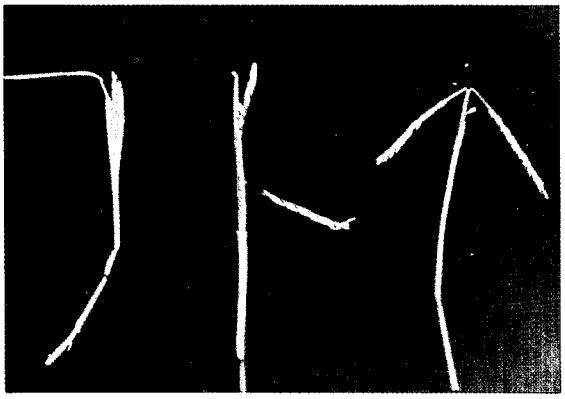
FIG. 8 is a photograph showing the opening stages of the spike from beginning through the deflexed stage at maturity.
Figure 9:
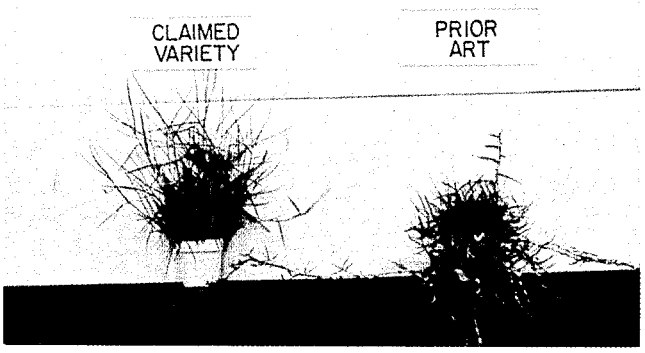
FIG. 9 is a photograph illustrating the difference in erect habit of the claimed variety and the closest known variety of the species.
Figure 10:
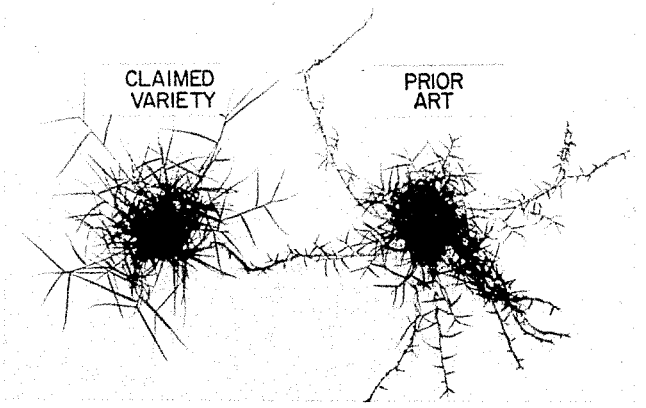
FIG. 10 is a photograph illustrating the spreading habit of the claimed variety compared to the closest known variety.
Figure 11:
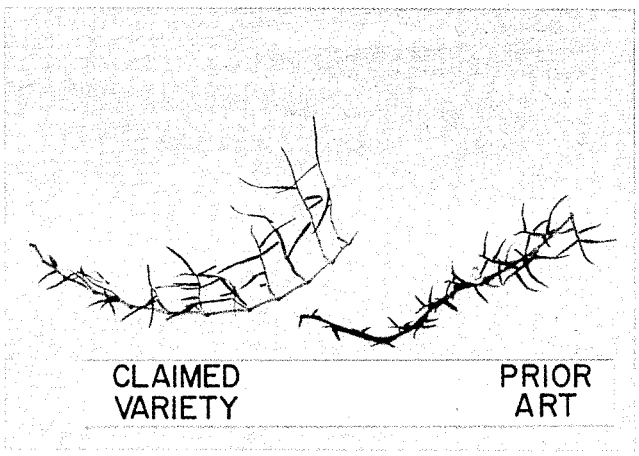
FIG. 11 is a photograph comparing a stolon of the claimed variety with a stolon of the closest known variety.
Figure 12:
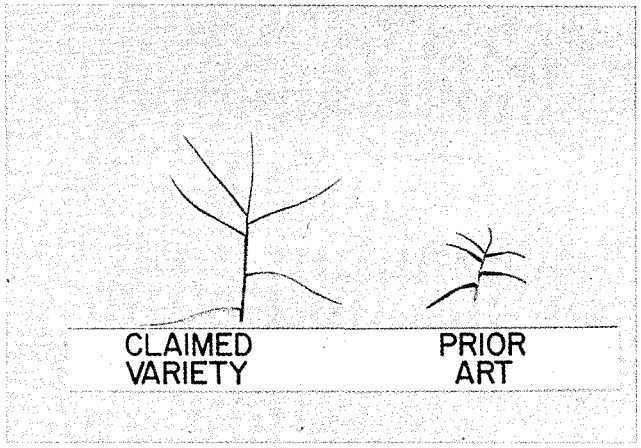
FIG. 12 is a photograph comparing a leaf of the claimed variety with a leaf of the closest known variety.

Having now described the new and distinct variety of *Paspalum vaginatum* grass plant which I have discovered and asexually reproduced.

I claim:

1. The variety of *Paspalum vaginatum* grass plant, substantially as described and illustrated.

No references cited.

ROBERT E. BAGWILL, Primary Examiner